(12) United States Patent
Golomb et al.

(10) Patent No.: US 7,008,645 B2
(45) Date of Patent: Mar. 7, 2006

(54) METHOD OF INHIBITING RESTENOSIS USING BISPHOSPHONATES

(75) Inventors: Gershon Golomb, Efrat (IL); Haim Danenberg, Brookline, MA (US)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 146 days.

(21) Appl. No.: 10/160,207

(22) Filed: May 30, 2002

(65) Prior Publication Data
US 2003/0013686 A1 Jan. 16, 2003

Related U.S. Application Data

(63) Continuation-in-part of application No. 10/126,248, filed on Apr. 19, 2002, which is a continuation-in-part of application No. 09/743,705, filed as application No. PCT/IL99/00387 on Jul. 14, 1999.

(30) Foreign Application Priority Data
Jul. 14, 1998 (IL) ...................................... 125336

(51) Int. Cl.
*A61K 9/14* (2006.01)
*A61K 9/127* (2006.01)
*A01N 57/00* (2006.01)

(52) U.S. Cl. .................. 424/489; 424/450; 514/75; 514/102; 514/824; 514/951

(58) Field of Classification Search ................ 424/400, 424/422, 423, 450, 484, 489, 490; 514/102, 514/103, 104, 106, 107, 108, 937
See application file for complete search history.

(56) References Cited

U.S. PATENT DOCUMENTS 4,067,971 A 1/1978 Francis et al.

(Continued)

FOREIGN PATENT DOCUMENTS

DE 196 37 890 A1 3/1998

(Continued)

OTHER PUBLICATIONS

Makkar et al, J. Cardiovascular Pharmacology Therapy, Apr. 1996, 1(2): 177-188.*

(Continued)

*Primary Examiner*—Gary Kunz
*Assistant Examiner*—Sharmila S Gollamudi
(74) *Attorney, Agent, or Firm*—Morgan & Finnegan LLP (57) ABSTRACT

A method of inhibiting the activity or production of cytokines or growth factors associated with vascular restenosis, by administering to an individual an effective amount of an active ingredient comprising a bisphosphonate particle or a bisphosphonate particulate. The bisphosphonate may be encapsulated, embedded or adsorbed within the particle, dispersed uniformly in the polymer matrix, adsorbed on the particle surface, or in combination of any of these forms. The particles include liposomes or inert polymeric particles, such as microcapsules, nanocapsules, nanoparticles, nanospheres, or microparticles. The particulates include any suspended or dispersed form of the bisphosphonate which is not encapsulated, entrapped, or adsorbed within a polymeric particle. The particulates include suspended or dispersed colloids, aggregates, flocculates, insoluble salts and insoluble complexes of the active ingredient. The cytokines and growth factors include, but are not limited to interleukin 1-β, matrix metalloproteinase-2, and platelet-derived growth factor β (PDGFβ).

17 Claims, 4 Drawing Sheets

U.S. PATENT DOCUMENTS

| | | | |
|---|---|---|---|
| 4,216,211 A | | 8/1980 | Francis |
| 4,997,454 A | * | 3/1991 | Violante et al. .......... 23/305 A |
| 5,096,717 A | | 3/1992 | Wirth et al. |
| 5,196,409 A | | 3/1993 | Breuer et al. |
| 5,312,954 A | | 5/1994 | Breuer et al. |
| 5,338,731 A | | 8/1994 | Breuer et al. |
| 5,492,926 A | * | 2/1996 | Cullinan et al. ............ 514/422 |
| 5,652,227 A | | 7/1997 | Teronen et al. |
| 5,733,564 A | | 3/1998 | Lehtinen |
| 5,741,514 A | | 4/1998 | Barenholz et al. |
| 5,760,030 A | | 6/1998 | Bryant et al. |
| 5,792,885 A | | 8/1998 | Ham et al. |
| 5,882,656 A | | 3/1999 | Bechard et al. |
| 5,932,563 A | | 8/1999 | Stokes et al. |
| 5,932,580 A | | 8/1999 | Levitzki et al. |
| 5,994,341 A | | 11/1999 | Hunter et al. |
| 6,030,639 A | * | 2/2000 | Janoff et al. ................ 424/450 |
| 6,139,871 A | | 10/2000 | Hope et al. |
| 6,306,421 B1 | * | 10/2001 | Kunz et al. ................. 424/423 |
| 2002/0192157 A1 | | 12/2002 | Low et al. |

FOREIGN PATENT DOCUMENTS

| | | |
|---|---|---|
| EP | 0 339 237 | 11/1989 |
| EP | 0459 318 | 12/1991 |
| WO | 97 33552 | 9/1997 |
| WO | 97 43437 | 11/1997 |
| WO | WO 97/43437 | * 11/1997 |
| WO | WO 88 00289 | 2/1998 |
| WO | 98 31359 | 7/1998 |
| WO | 99 38998 | 8/1999 |
| WO | 00 21540 | 10/1999 |
| WO | 00 34293 | 6/2000 |
| WO | 00 64516 | 11/2000 |

OTHER PUBLICATIONS

Abstract, Kunitomo et al., "Experimental Induction of Athero Sclerosis in Guinea-Pigs Fed a Cholesterol Vitamin D-2-Rich Diet", (1983).

Mönkkönen et al., "The Effect of Liposome-Encapsulated and free Clodronate on the Growth of Macrophage-like Cells In Vitro: The Role of Calcium and Iron", Calcif. Tissue International, (1993), vol. 53, pp. 139-146.

Kramsch et al., "The Effect of Agents Interfering with Soft Tissue Calcification and Cell Proliferation on Calcific Fibrous-Fatty Plaques in Rabbits", Circulation Research, (1978), vol. 42, No. 4, pp. 562-570.

Mönkkönen et al., "Growth Inhibitions of Macrophage-Like and Other Cell Types by Liposome-Encapsulated, Calcium-Bound, and Free Bisphosphonates In Vitro", Journal of Drug Targeting, (1994), vol. 2, pp. 299-308.

Fleisch, "Bisphophonates in bone disease", Parthenon Publishing Group Inc., (1997), pp. 184-210.

Mak et al., "Clinical Trials to Prevent Restenosis after Percutaneous Coronary Revescularization", The NY Academy of Sciences, (1994), pp. 225-277.

LeClerc et al., "Drug Prevention of Restenosis After Angioplasty: an Update", Elsevier Science, (1995), pp. 722-724.

Lefkovits et al., "Pharmacological Approaches for the Prevention of Restenosis After Percutaneous Coronary Intervention", Progress in Cardiovascular Disease, (1997), vol. 40, No. 2, pp. 141-158.

Hamon et al., "Restenosis after Coronary Angioplasty", European Heat Journal, (1995), vol. 16, pp. 33-48.

Gottsauner-Wolf et al., "Influence of local delivery of the protein tyrosine kinase receptor inhibitor tyrphostin-47 on smooth-muscle cell proliferation in a rat carotid balloon-injury model", American Heart Journal (1996), vol. 19, pp. 347-356.

Shioi et al., "β-Glycerophosphate Accelerates Calcification in Cultured Bovine Vascular Smooth Muscle Cells", Arteriosclerosis, Thrombosis and Vascular Biology, (1995), vol. 15, No. 11, pp. 2003-2009.

Paspaliaris et al., "Clodronate Inhibits Contraction and Prevents the Action of L-Type Calcium Channel Antagonists in Vascular Smooth Muscle", (1991), Journal of Bone and Mineral Research, vol. 6, No. 8, pp. 835-841.

Bellah et al., "Idiopathic arterial calcification of infancy: Prenatal and postnatal effects of therapy in an infant", (1992), The Journal of Pediatrics, vol. 121, No. 6, pp. 930-933.

Waller et al., "Coronary Artery and Sapheous Vein Graft Remodeling: A Review of Histologic Findings After Various Interventional Procedure—Part VI", Clin. Cardiol., (1997), vol. 20, pp. 153-160.

Anderson et al., "A Review of Randomized Trials Comparing Coronary Angioplasty and Bypass Grafting", Curr-Opin-Cardiol, (1996), vol. 11, No. 6, pp. 583-590.

Moorman et al., "Percutaneous Transluminal Coronary Angioplasty (PTCA): Long-term Outcome and Aeromedical Implications", Aviation, Space and Enviromental Medicine, (1996), vol. 67, No. 10, pp. 990-996.

Laurent et al., "The Arterial Wall: A New Pharmacological and Therapeutic Target", Fundam Clin Pharmacol, (1996), vol. 10, pp. 243-257.

Schwartz, "The Vessel Wall Reaction in Restenosis", Semin-Interv-Cardiol, (1997), vol. 2, pp. 83-88.

Allaire et al., "Endothelial Cell Injury in Cardiovascular Surgery: The Intimal Hyperplastic Reponse", Ann Thorac Surg, (1997), vol. 63, pp. 582-591.

Webb et al., "Inhibition of Bioprosthetic Heart Valve Calcification with Aminodiphosphonate Covalently Bound to Residual Aldehyde Groups", Ann Thorac Surg., (1988), vol. 46, pp. 309-316.

Wagner et al., "Contrasting Effects of Ethane-1-Hydroxy-1, 1-Diphosphonate (EHDP) on the Regression of two types of Dietary-Induced Atherosclerosis", Atherosclerosis, (1977), vol. 27, pp. 419-435.

Daoud et al., "The effect of ethane-1-hydroxy-1, 1-diphosphonate (EHDP) on Necrosis of Atherosclerotic Lesions", Atherosclerosis, (1987), vol. 67, pp. 41-48.

Walsh et al., "Molecular Strategies to Inhibit Testenosis: Modulation of the Vacular Myocyte Phenotype", Semin Intervent Cardiol, (1996), vol. 1, pp. 173-179.

Hermann et al., "Pharmacological Approaches to the Prevention of Restenosis Following Angioplasty", DRUG, (1993), vol. 46, No. 1, pp. 18-52.

Rubin et al., "Cellular and Molecular Mechanisims of Radiation Inhibition of Restenosis. Part I: Role of te Macrophage and Platelet-Derived Growth Factor", Int. J. Radiation Oncology Biol. Phys. (1998), vol. 40, pp. 929-941.

Monkkonen et al., "Studies on Liposome Formulations for Intra-articular Delivery of Clodronate", Journal of Controlled Release, (1995), vol. 35, pp. 145-154.

Ylitalo, 2002, "Bisphosphonates and atherosclerosis" General Pharmacology 35:287-296.

* cited by examiner

| Treatment type | Animal (No.) | Dosing days | N/M | % stenosis |
|---|---|---|---|---|
| Empty liposomes | Rat (20) | -1, +6 | 1.62 ± 0.1 | 44.5 ± 2.0 |
| Clodronate | Rat (10) | -1, +6 | 1.2 ± 0.2 | 40.2 ± 7.2 |
| Liposomal clodronate 15 mg/kg | Rat (10) | -1 | 0.45 ± 0.1 | 15.4 ± 3.4 |
| Liposomal clodronate 15 mg/kg | Rat (10) | -1, + 6 | 0.35 ± 0.07 | 12.0 ± 2.3 |
| Empty liposomes | Rabbit (10) | -1 | 1.94 ± 0.3 | 86.6 ± 4.0 |
| Liposomal clodronate 10 mg/kg | Rabbit (10) | -1 | 1.11 ± 0.2 | 71.5 ± 2.1 |
| Silica particles 1000 mg/kg | Rat (10) | -1 | 0.8 ± 0.1 | 24.2 ± 3.8 |

METHOD OF INHIBITING RESTENOSIS USING BISPHOSPHONATES

This application is a continuation in part of co-pending application Ser. no. 10/126,248 filed on Apr. 19, 2002, which is a continuation-in-part of co-pending application Ser. No. 09/743,705 filed on Mar. 22, 2001, which is a 35 U.S.C §371 filing of PCT application No. PCT/IL99/00387 filed on Jul. 14, 1999, which is a continuation-in-part of Israeli application no. 125336 filed on Jul. 14, 1998.

FIELD OF THE INVENTION

The present invention is concerned with compositions capable of preventing, inhibiting or reducing restenosis (sometimes referred to in the art as "accelerated arteriosclerosis" and "post-angioplasty narrowing"). Specifically, the invention relates to the use of bisphosphonates ("BP") to inhibit and/or prevent restenosis.

BACKGROUND OF THE INVENTION

Over the past decade, mechanical means of achieving revascularization of obstructive atherosclerotic vessels have been greatly improved. Percutaneous transluminal coronary angioplasty (PTCA) procedures include, but are not limited to, balloon dilatation, excisional atherectomy, endoluminal stenting, rotablation and laser ablation. However, revascularization induces thrombosis, and neointimal hyperplasia, which in turn cause restenosis in a substantial proportion of coronary arteries after successful balloon angioplasty and in aortacoronary saphenous vein bypass graft and other coronary grafts. Furthermore, intimal hyperplasia causes restenosis in many superficial femoral angioplasties, carotid endarterectomies, and femoro-distal vein bypasses. Restenosis is the formation of new blockages at the site of the angioplasty or stent placement or the anastomosis of the bypass. As a result, the patient is placed at risk of a variety of complications, including heart attack or other ischemic disease, pulmonary embolism, and stroke. Thus, such procedures can entail the risk of precisely the problems that its use was intended to ameliorate. The introduction of endovascular stents has reduced the incidence of restenosis, but this problem still remains significant, since restenosis or "over exuberant" tissue healing may occur at the site of stent placement. (Waller, B. F. et al., 1997, *Clin-Cardiol.*, 20(2): 153–60; Anderson, W. D et al., 1996, *Curr-Opin-Cardiol.*, 11(6):583–90; Moorman, D. L. et al., 1996, *Aviat-Space-Environ-Med.*, 67(10):990–6; Laurent, S. et al., 1996, *Fundam. Clin. Pharmacol.* 10(3):243–57; Walsh, K. et al., 1996, *Semin-Interv-Cardiol.*, 1(3):173–9; Schwartz, R. S., 1997, *Semin-Interv-Cardiol.*, 2(2):83–8; Allaire, E. et al., 1997, *Ann. Thorac. Surg.*, 63:582–591; Hamon, M. et al., 1995, *Eur. Heart J.*, 16:33s–48s; Goffsauner-Wolf, M., et al., 1996, *Clin. Cardiol.*, 19:347–356).

Despite extensive research on the incidence, timing, mechanisms and pharmacological interventions in humans and animal models to date, no therapy exists which consistently prevents coronary restenosis (Herrman, J. P. R. et al., 1993, *Drugs*, 46:18–52; Leclerc, G. et al., 1995, *Elsevier Science*, 722–724, Topol, E., 1997, *The NY Academy of Sciences*, 225–277). Compositions and methods for the reduction or prevention of restenosis are still greatly desired. Accordingly, it would be desirable to develop novel compositions and methods that are effective in treating restenosis and preventing its reoccurrence.

Bisphosphonates ("BPs") (formerly called diphosphonates) are compounds characterized by two C—P bonds. If the two bonds are located on the same carbon atom (P—C—P) they are termed geminal bisphosphonates. The BPs are analogs of the endogenous inorganic pyrophosphate which is involved in the regulation of bone formation and resorption. The term bisphosphonates is generally used for geminal and non-geminal bisphosphonates. The BPs may at times form polymeric chains. BPs act on bone because of their affinity for bone mineral and also because they are potent inhibitors of bone resorption and ectopic calcification. BPs have been clinically used mainly as (a) antiosteolytic agents in patients with increased bone destruction, especially Paget's disease, tumor bone disease and osteoporosis; (b) skeletal markers for diagnostic purposes (linked to $^{99m}$Tc); (c) inhibitors of calcification in patients with ectopic calcification and ossification, and (d) antitartar agents added to toothpaste (Fleisch, H., 1997, in: Bisphosphonates in bone disease. Parthenon Publishing Group Inc., 184–186). Furthermore, being highly hydrophilic and negatively charged, BPs in their free form are almost incapable of crossing cellular membranes.

SUMMARY OF THE INVENTION

In one embodiment, the present invention relates to a method of treating or preventing restenosis by administering to an individual an effective amount of an active ingredient comprising a bisphosphonate, a bisphosphonate salt, a bisphosphonate ester, or a bisphosphonate complex, wherein the active ingredient is in a particle dosage form. The particles include, but are not limited to, inert polymeric particles, such as microcapsules, nanocapsules, nanospheres, microspheres, nanoparticles, microparticles, or liposomes.

In a further embodiment, the present invention relates to a method of treating or preventing restenosis by administering to an individual an effective amount of an active ingredient comprising a bisphosphonate, an insoluble bisphosphonate salt, an insoluble bisphosphonate ester, or an insoluble bisphosphonate complex, wherein the active ingredient is in a free particulate dosage form.

Effective phagocytosis of both the bisphosphonate particles and the bisphosphonate free particulates by the monocytes/macrophages can affect the activity of such phagocytic cells. The active ingredient affects restenosis by inhibiting phagocytic cells involved in the restenotic cascade, such as macrophages/monocytes and fibroblasts. The delivery system affects smooth-muscle cells (SMC) and extracellular matrix production indirectly by inhibiting the cells that trigger their migration and/or proliferation. Nevertheless, a direct effect on SMC may also occur. The active ingredient may be administered by any route which effectively transports the active compound to the desirable site of action. In a preferred embodiment, the mode of administration includes intra-arterial, intravenous or subcutaneous administration.

In a further embodiment, the present invention includes a method of treating or preventing restenosis by administering to an individual, an effective amount of any compound or composite known to inactivate or inhibit blood monocytes and tissue macrophages, thereby treating or preventing restenosis.

In a further embodiment, the present invention includes a pharmaceutical composition comprising an active ingredient selected from the group consisting of a bisphosphonate particle, a bisphosphonate particulate, or a salt, ester, or complex of bisphosphonate, together with a pharmaceutically acceptable carrier, stabilizer or diluent for the prevention or treatment of vascular restenosis.

In yet a further embodiment, the present invention includes a method of inhibiting the activity and/or production of cytokines and growth factors associated with vascular restenosis, by administering an effective amount of an active ingredient comprising a bisphosphonate, a bisphosphonate salt, a bisphosphonate ester, or a bisphosphonate complex, wherein the active ingredient is in a particle dosage form.

In still yet a further embodiment, the present invention includes a method of inhibiting the activity and/or production of cytokines and growth factors associated with vascular restenosis, by administering to an individual an effective amount of an active ingredient comprising a bisphosphonate, an insoluble bisphosphonate salt, an insoluble bisphosphonate ester, or an insoluble bisphosphonate complex, wherein the active ingredient is in a free particulate dosage form.

BRIEF DESCRIPTION OF THE DRAWINGS

FIG. 1 shows the mean neointimal area to the area of the media in rats treated with clodronate containing liposomes as compared to rats treated with control liposomes. The medial area is the difference between the total arterial area and the original lumen area.

FIG. 2 shows the % stenosis in rats treated with clodronate containing liposomes as compared to the % stenosis in rats treated with control liposomes.

FIG. 3 shows the extent of medial area as an indirect index of smooth muscle cell viability and determined as the difference between the total arterial area and the original lumen area (External elastic lamina bound area—Internal elastic lamina bound area) in rats treated with clodronate containing liposomes as compared to rats treated with control liposomes only.

FIGS. 5a and 5b illustrate the effect of liposomal clodronate treatment on IL-1β concentration in the rat and rabbit models, respectively, and FIGS. 5c and 5d illustrate the effect of liposomal clodronate treatment on MMP-2 activity in the rat and rabbit models, respectively.

FIG. 7a illustrates the effect on platelet-derived growth factor β receptor (PDGFβR) activation (i.e., tyrosine phosphorylation), FIG. 7b illustrates the effect on the PDGFβBR protein, and FIG. 7c illustrates the effect on the PDGF-B protein.

DETAILED DESCRIPTION OF THE INVENTION

The present invention relates to compositions and methods for reducing, delaying or eliminating restenosis. Reducing restenosis includes decreasing the thickening of the inner blood vessel lining that results from stimulation and proliferation of smooth muscle cell and other cell migration and proliferation, and from extracellular matrix accumulation, following various angioplasty procedures. Delaying restenosis includes delaying the time until angiographic re-narrowing of the vessel appears or until the onset of clinical symptoms which are attributed to stenosis of this vessel. Eliminating restenosis following angioplasty includes reducing hyperplasia to an extent which is less than 50% of the vascular lumen, with lack of clinical symptoms of restenosis. Methods of intervening include re-establishing a suitable blood flow through the vessel by methods such as, for example, repeat angioplasty and/or stent placement, or coronary artery bypass graft (CABG).

The present invention includes a method of treating or preventing restenosis by administering to an individual, an effective amount of any compound or composite known to inactivate or inhibit blood monocytes and tissue macrophages.

One example of a group of drugs useful in the present invention to inhibit restenosis, are bisphosphonates ("BPs"). BPs inhibit smooth muscle cell migration and proliferation by transiently depleting and/or inactivating cells that are important triggers in the restenosis cascade, namely macrophages and/or monocytes. Bisphosphonates, when encapsulated in liposomes or nanoparticles in a "particle" dosage form, or when in a "free particulate" dosage form, such as, for example, in aggregates of a specific size, are taken-up, by way of phagocytosis, very efficiently by the macrophages and monocytes, and to some extent by other cells with phagocytic activity such as fibroblasts. Once inside the macrophages, the liposomal structure of the cell is disrupted and the bisphosphonates are released, thereby inhibiting the activity and/or killing the macrophages. Since macrophages, in their normal state, are recruited to the areas traumatized by angioplasty or other intrusive intervention and initiate the proliferation of smooth-muscle cells (SMC), inhibiting the macrophages' activity inhibits the migration and proliferation of SMC. After being taken-up by the macrophages, the bisphosphonates have a sustained inhibitory activity on the macrophages. Thus, prolonged release of the bisphosphonates is not required in order to sustain inhibition. Accordingly, the method of inhibiting or reducing restenosis by administering a bisphosphonate in a particle or free particulate form is preferably a systemic therapy, in that the bisphosphonate particles and particulates target the circulating monocytes and macrophages.

It should be noted, however, that some bisphosphonate particles and particulates may have a direct effect on SMC activity. Additionally, some of the bisphosphonate particles and particulates may also inactivate other phagocytic cells and cells of the white-blood cell lineage in the body, such as liver and spleen macrophages and macrophages in the arterial walls.

Furthermore, the delivery system of the present invention not only retains the BP for a sufficient time so that the free BP is not released in the body fluids, but also efficiently discharges the drug within the target cell. The free BP drug, as opposed to BP particles, is ineffective since it is not taken-up by phagocytic cells.

An additional example of a group of drugs useful in the present invention to inhibit restenosis are inactivators of monocytes/macrophages, such as gallium or gold.

In accordance with the present invention, a bisphosphonate or a compound or composite which inactivates monocytes/macrophages (collectively herein: "active ingredient") is used for treatment or prevention of vascular restenosis. The term bisphosphonate as used herein, denotes both geminal and non-geminal bisphosphonates. The term "active ingredient" encompasses in its scope, not only BP and compounds which inactivate monocytes/macrophage, but also polymeric chains of the BPs and the monocyte/macrophage inactivators, particularly such chains consisting of up to 40 BP monomers. Preferred active ingredients are compounds of the following formula (I)

wherein $R_1$ is H, OH or a halogen atom; and $R_2$ is halogen; linear or branched $C_1$–$C_{10}$ alkyl or $C_2$–$C_{10}$ alkenyl optionally substituted by heteroaryl or heterocyclyl $C_1$–$C_{10}$ alkylamino or $C_3$–$C_8$ cycloalkylamino where the amino may be a primary, secondary or tertiary; —NHY where Y is hydrogen, $C_3$–$C_8$ cycloalkyl, aryl or heteroaryl; or $R_2$ is —SZ where Z is chlorosubstituted phenyl or pyridinyl.

The present invention thus provides the use of said active ingredient, a complex of said active ingredient or a pharmaceutically acceptable salt or ester thereof for the preparation of a composition for the prevention or treatment of vascular restenosis. In one embodiment, the composition comprises a "particle" dosage form, wherein the active ingredient is encapsulated, embedded, and/or adsorbed within a particle, dispersed in the particle matrix, adsorbed or linked on the particle surface, or in combination of any of these forms. The particle includes any of the liposomes, microparticles, nanoparticles, nanospheres, microspheres, microcapsules, or nanocapsules known in the art (M. Donbrow in: Microencapsulation and Nanoparticles in Medicine and Pharmacy, CRC Press, Boca Raton, Fla., 347). The term particle includes both polymeric and non-polymeric preparations of the active ingredient. In a further embodiment, the composition comprises a "free particulate" dosage form of the active ingredient, such as an insoluble salt, insoluble ester, or insoluble complex of the active ingredient. Typically, "insoluble" refers to a solubility of one (1) part of a compound in more than ten-thousand (10,000) parts of a solvent. A "free particulate" dosage form includes any insoluble suspended or dispersed particulate form of the active ingredient which is not encapsulated, entrapped or adsorbed within a polymeric particle. Free particulates include, but are not limited to, suspended or dispersed colloids, aggregates, flocculates, insoluble salts and insoluble complexes. Additionally, in both the particle and free particulate dosage forms, suspending agents and stabilizers may be used. In yet a further embodiment, the composition comprises polymeric chains of the active ingredient.

The present invention also provides a method of treatment of restenosis, comprising administering to an individual in need an effective amount of said active ingredient, a complex thereof or a pharmaceutically acceptable salt or ester thereof.

The present invention still further provides a pharmaceutical composition for the prevention or treatment of restenosis comprising, an effective amount of the active ingredient, a complex or a salt thereof, optionally together with a pharmaceutically acceptable carrier or diluent. Carriers include, but are not limited to, liposomes, particles, and lipid particles.

The present invention also provides a method of inhibiting the activity, production, and/or transcription of certain cytokines and growth factors that are associated with restenosis or with any of the cell types involved in the restenotic cascade, by administering a bisphosphonate particle or particulate. The select cytokines and growth factors that are associated with restenosis or with the cell types involved in the restenotic cascade include, but are not limited to, interleukin-1 (IL-1), matrix metalloproteinases (MMPs), and platelet-derived growth factor β (PDGFβ). For example, IL-1β, and MMP-2 are major products of activated macrophages, that are secreted following arterial injury, and contribute to the process of neointimal proliferation. Additionally, PDGF-BB is a strong chemoattractant for vascular smooth muscle cells and is involved in neointima formation secondary to vascular injury. (Fishbein, I., et al., 2000, *Arterioscler. Thromb. Vasc. Biol.,* 20:667–676; Jawien, A., et al., 1992, *J. Clin. Invest.,* 507–511; Ross, R., 1993, *Nature,* 362:801–809; Panek, R. L., et al., 1997, *Arterioscler. Thromb. Vasc. Biol.,* 17:1283–1288; Waltenberger, J, 1997, *Circulation,* 96:4083–4094; Deguchi, J., et al., 1999, *Gene Ther.,* 6:956–965.)

The term "effective amount" denotes an amount of the active ingredient, which is effective in achieving the desired therapeutic result, namely prevention, reduction, or elimination of vascular restenosis. The effective amount may depend on a number of factors including: weight and gender of the treated individual; the type of medical procedure, e.g. whether the vascular restenosis to be inhibited is following balloon angioplasty, balloon angioplasty followed by deployment of a stent; the mode of administration of the active ingredient (namely whether it is administered systemically or directly to the site); the type of carrier being used (e.g. whether it is a carrier that rapidly releases the active ingredient or a carrier that releases it over a period of time); the therapeutic regime (e.g. whether the active ingredient is administered once daily, several times a day, once every few days, or in a single dose); clinical factors influencing the rate of development of restenosis such as diabetes, smoking, hypercholesterolemia, renal diseases; anatomical factors such as whether there is severe preangioplasty stenosis, total occlusion, left anterior descending coronary artery location, saphenous vein graft lesion, long lesions, multivessel or multilesion PTCA; and on the dosage form of the composition. Moreover, procedural variables may also have bearing on the dosage, such as greater residual stenosis following PTCA, severe dissection, intimal tear, appropriate size of balloon, and the presence of thrombus. The artisan, by routine type experimentation should have no substantial difficulties in determining the effective amount in each case.

The invention is applicable for the prevention, reduction or treatment of vascular restenosis and mainly, but not limited to, coronary restenosis after angioplasty. Vascular restenosis primarily results from various angioplasty procedures including balloon angioplasty, intravascular stent deployment or other methods of percutaneous angioplasty

(including angioplasty of coronary arteries, carotid arteries, and other vessels amenable for angioplasty) as well as for restenosis resulting from vascular graft stenosis (e.g. following by-pass surgery) (Braunwald, E., 1997, *Heart Disease* in: A textbook of cardiovascular medicine; 5th Ed., W. B. Saunders Company: Philadelphia).

In addition, the invention is also applicable for use in prevention, reduction or treatment of vascular restenosis in peripheral arteries and veins.

One exemplary application of the invention is to prevent and treat in-stent restenosis. It is a widely acceptable medical procedure to deploy a stent within a blood vessel within the framework of an angioplastic procedure, to support the walls of the blood vessel. However, very often restenosis occurs notwithstanding the presence of the stent within the blood vessel. In accordance with the invention, the above noted active ingredient may be administered, either systemically or directly to the site, in order to prevent or inhibit such restenosis. The active ingredient may be formulated in a manner allowing its incorporation onto the stent which, in fact, yields administration of said active ingredient directly at the site. The active ingredient may be formulated in that manner, for example, by including it within a coating of the stent. Examples of coatings are polymer coatings, (e.g., made of polyurethane), gels, fibrin gels, hydrogels, carbohydrates, gelatin, or any other biocompatible gel.

The active ingredient used in accordance with the invention may be formulated into pharmaceutical compositions by any of the conventional techniques known in the art (see for example, Alfonso, G. et al., 1995, in: The Science and Practice of Pharmacy, Mack Publishing, Easton Pa., 19th ed.). The compositions may be prepared in various forms suitable for injection, instillation or implantation in body such as suspensions of the nanoparticles, as in a coating of a medical device such as a stent (see above). In addition, the pharmaceutical compositions of the invention may be formulated with appropriate pharmaceutical additives for parental dosage forms. The preferred administration form in each case depends on the desired delivery mode, which is usually that which is the most physiologically compatible with the patient's condition and with the other therapeutic treatments which the patient currently receives.

In a preferred embodiment of the invention, the active ingredient is selected from the group of bisphosphonates. One preferred active ingredient for this group is the compound clodronate, (dichloromethylene) diphosphonic acid, (Fleisch, H., 1997, in: Bisphosphonates in bone disease. Parthenon Publishing Group Inc., 184–186) having the following formula (II):

(II)

Clodronate was previously described for use in the treatment of hypercalcemia resulting from malignancy in the treatment of tumor associated osteolysis (Fleisch, H., 1997, in: Bisphosphonates in bone disease. Parthenon Publishing Group Inc., 184–186). Clodronate was also found to inhibit macrophages in vitro and to suppress macrophage activity in the spleen and liver tissues of mice. (Mönkkönen, J. et al, 1994, *J. Drug Target*, 2:299–308; Mönkkönen, J. et al., 1993, *Calcif. Tissue Int.*, 53:139–145).

Other preferred active ingredients of this group are etidronate and tiludronate having the following formulae (III) and (IV) respectively:

(III)

(IV)

Additional BPs having activities similar to that of clodronate are also preferred in accordance with the invention. Such BPs may be selected on the basis of their ability to mimic the biological activity of clodronate. This includes, for example: in vitro activity in inhibiting phagocytic activity of phagocytic cells, e.g. macrophages and fibroblasts; inhibition of secretion of IL-1 and/or IL-6 and/or TNF-α from macrophages; reduction of MMP activity, for example, MMP-2 activity; inhibition of PDGFβR activation and/or reduction of PDGF-B protein levels; and, in vivo activity, e.g. the ability of the tested BP to prevent or reduce restenosis in an experimental animal model such as, for example, the rat or rabbit carotid catheter injury model described in Example 1 below, or porcine model of restenosis.

The most preferred group of active ingredients in accordance with the invention are the amino-BPs and any other nitrogen-containing BPs having the following general formula (V):

(V)

wherein X represents $C_1$–$C_{10}$ alkylamino or $C_3$–$C_8$ cycloalkylamino, where the amino may be primary, secondary or tertiary; or X represents NHY where Y is hydrogen, $C_3$–$C_8$ cycloalkyl, aryl or heteroaryl.

The BPs belonging to this group are believed not to be metabolized and have been shown at relatively low concentrations to induce secretion of the interleukin, IL-1, and cause, at relatively high concentrations, apoptosis in macrophages (Mönkkönen, J. et al., 1993, *Calcif. Tissue Int.*, 53:139–145). Preferred BPs belonging to this group are for example, pamidronate and alendronate having the following formulae (VI) and (VII), respectively.

Although the geminal BPs are preferred BPs in accordance with the invention, non-geminal BPs, monophosphonates of BPs, termed generally as phosphonates may also be used as active ingredients in accordance with the invention.

Additional bisphosphonates include, but are not limited to, 3-(N,N-dimethylamino)-1-hydroxypropane-1,1-diphosphonic acid, e.g. dimethyl-APD; 1-hydroxy-ethylidene-1,1-bisphosphonic acid, e.g. etidronate; 1-hydroxy-3(methylpentylamino)-propylidene-bisphosphonic acid, (ibandronic acid), e.g. ibandronate; 6-amino-1-hydroxyhexane-1,1-diphosphonic acid, e.g. amino-hexyl-BP; 3-(N-methyl-N-pentylamino)-1-hydroxypropane-1,1-diphosphonic acid, e.g. methyl-pentyl-APD; 1-hydroxy-2-(imidazol-1-yl)ethane-1,1-diphosphonic acid, e.g. zoledronic acid; 1-hydroxy-2-(3-pyridyl)ethane-1,1-diphosphonic acid (risedronic acid), e.g. risedronate; 3-[N-(2-phenylthioethyl)-N-methylamino]-1-hydroxypropane-1,1-bishosphonic acid; 1-hydroxy-3-(pyrrolidin-1-yl)propane-1,1-bisphosphonic acid, 1-(N-phenylaminothiocarbonyl)methane-1,1-diphosphonic acid, e.g. FR 78844 (Fujisawa); 5-benzoyl-3,4-dihydro-2H-pyrazole-3,3-diphosphonic acid tetraethyl ester, e.g. U81581 (Upjohn); and 1-hydroxy-2-(imidazo[1,2-a]pyridin-3-yl)ethane-1,1-diphosphonic acid, e.g. YM 529.

Thus, suitable bisphosphonates for use in the present invention include the acid compounds presented above, any acceptable salts thereof, and crystalline and amorphous BPs. Additionally, preferred bisphosphonates are the amino-bisphosphonates such as alendronate, zolendronate, and risendronate.

The composition of the invention may comprise said active ingredient either encapsulated within a particle, adsorbed on the particle surface, complexed with metal cations such as calcium, magnesium or organic bases, formed into non-soluble salts or complexes, or polymerized to yield polymers of up to 40 monomers. The salts may be sodium, potassium, ammonium, gallium or calcium salts or salts formed with any other suitable cation (e.g. organic amino compounds). The salts or polymers may be in a micronized particulate form having a diameter within the range of about 0.01–1.0 μm, preferably within a range of about 0.1–0.5 μm. The active ingredients in their salt form may be with or without water of crystallization (hydrous and anhydrous). Additionally, additives such as polyvinyl alcohol (PVA), pluronics, and other surface active agents, may be used to stabilize the salt or complex to establish a colloidal or nano-size suspension. In one embodiment for example, the composition may comprise a Ca—BP salt and or complex.

In one embodiment of the invention, the active ingredient is encapsulated in liposomes. The liposomes may be prepared by any of the methods known in the art (regarding liposome preparation methods see Mönkkönen, J. et al, 1994, *J. Drug Target*, 2:299–308, and Mönkkönen, J. et al., 1993, *Calcif. Tissue Int.*, 53:139–145). The liposomes may be positively charged, neutral or negatively charged (negatively charged liposomes being currently preferred), and may be single or multilamellar. Suitable liposomes in accordance with the invention are preferably non toxic liposomes such as, for example, those prepared from phosphatidylcholine phosphoglycerol, and cholesterol, e.g. as described below. In many cases, use of liposomal delivery results in enhanced uptake of the active ingredient by cells not only via endocytosis but also via other pathways such as fusion (such uptake may play a role in the therapeutic effect). The diameter of the preferred liposomes may range from 0.15 to 300 nm. However, this is merely a non-limiting example, and liposomes of other size ranges may also be used.

In a further preferred embodiment, the active ingredient or bisphosphonate may be encapsulated or embedded in inert particles. In yet a further embodiment, the active ingredient may be adsorbed onto the surface of, or adsorbed within, a blank particle, wherein a blank particle is a particle which has no drug encapsulated or embedded therein. Alternatively, the active ingredient may form a particulate, which includes a colloid, aggregate, flocculate or other such structure known in the art for the preparation of particulates of drugs. Furthermore, such particulates may be aggregates of the polymerized active ingredient.

Particulates of the active ingredient may be obtained by using an insoluble salt or complex that can be obtained in-situ, i.e., starting with the soluble drug and "salting-out" the drug by adding for example, Ca at the appropriate concentration and pH. The dispersed or free particulates are formed and then stabilized by the aid of surface active agents, suspending agents, deflocculating agents or by thickening agents, such those used in gels. The active ingredient may be further precipitated by adding a trivalent cation, for example, gallium, thereby forming a precipitate of gallium-BP salt/complex.

The active ingredient may be encapsulated within or adsorbed onto particles, e.g., nanoparticles by utilizing, for example, a modified nano-precipitation method. In this embodiment of the invention, the polymeric nanoparticle containing the active ingredient is formed by mixing water and organic solutions of the drug and polymer (PLGA or other polymers), respectively. Thus, the nanoparticle containing drug formed is suspended in water and can be lyophilized. Additionally, the active ingredient may be entrapped or adsorbed into blank polymeric nanoparticles, and/or adsorbed on the surface of the blank polymeric nanoparticles. (Blank nanoparticles are particles which have no drug encapsulated, embedded, and/or adsorbed therein).

One advantage of particulate dosage forms of the active ingredient itself, or of polymeric particle dosage forms (e.g. nanoparticles), is the possibility of lyophilization and of sterilization methods other than filter-sterilization. Thus, these forms of the active ingredient have an extended shelf-life and ease of handling.

In a further embodiment, the bisphosphonates may be encapsulated in nanoparticles ("NP"). Nanoparticles are 30–1000 nm diameter, spherical or non-spherical polymeric particles. The drug can be encapsulated in the nanoparticle, dispersed uniformly or non-uniformly in the polymer matrix (monolithic), adsorbed on the surface, or in combination of any of these forms. It is the submicron nature of this compositional form, which makes it more efficient in therapeutic applications. The submicron size facilitates uptake by phagocytic cells such as monocytes and macrophages, and avoids uptake in the lungs. In a preferred embodiment, the polymer used for fabricating nanoparticles is the biocompatible and biodegradable, poly(DL-lactide-co-glycolide) polymer (PLGA). However, any polymer which is biocompatible and biodegradable may be used. Therefore, additional polymers which may be used to fabricate the NP include, but are not limited to, polyanhydrides, polyalkylcyanoacrylates (such as polyisobutylcyanoacrylate), polyetheyleneglycols, polyethyleneoxides and their derivatives, chitosan, albumin, gelatin and the like. The size of the nanoparticle used to encapsulate the active ingredient or bisphosphonate depends on the method of preparation and the mode of administration (e.g. IV, IA, etc.) Preferably, the nanoparticles range in size from 70–500 nm. However, depending on preparation and sterilization techniques, the more preferred ranges include, but are not limited to, 100–300 nm and 100–220 nm.

The pharmaceutical carrier or diluent used in the composition of the invention may be any one of the conventional solid or liquid or semisolid carriers known in the art. A solid carrier, for example, may be lactose, sucrose, gelatins, and other carbohydrates. A liquid carrier, for example, may be a biocompatible oil suitable for injection such as peanut oil, water or mixtures of biocompatible liquids, or a biocompatible viscous carrier such as a polyethylene or gelatin gel.

The composition of the active ingredient used for injection may be selected from emulsions, suspensions, colloidal solutions containing suitable additives, and additional suitable compositions known to the skilled artisan.

The compositions of the invention may be administered by any route which effectively transports the active compound to the appropriate or desirable site of action. By a preferred embodiment of the invention, the modes of administration are intravenous (IV) and intra-arterial (IA) (particularly suitable for on-line administration). Other suitable modes of administration include intramuscular (IM), subcutaneous (SC), or intraperitonal (IP). Such administration may be bolus injections or infusions. The compositions may also be administered locally to the diseased site of the artery, for example, by means of a medical device which is coated with the active ingredient. Another mode of administration may be by perivascular delivery. Combinations of any of the above routes of administration may also be used in accordance with the invention.

The dosage of the active ingredient to be used also depends on the specific activity of the active ingredient selected, on the mode of administration (e.g. systemic administration or local delivery), the form of the active ingredient (e.g. polymer, encapsulated in a particle such as a liposome, nanoparticle etc.), the size of the particle, the type of bisphosphonate, the administration route, the number of injections, the timing of injections, the biology/pathology of the patient in need, and other factors as known per se.

In one embodiment, the dosage for clodronate-containing liposomes (liposomal clodronate, ("LC")) in humans preferably ranges from 0.015 mg/kg (per kg of body weight) to 150 mg/kg; more preferably, however, the dosage ranges from 0.15 to 15 mg/kg. Dosages outside these preferred ranges may also be used, as can be readily determined by the skilled artisan. When IV/IA injections or local delivery methods are used, i.e. via a balloon catheter, the dosage is at the lower end of the range. However, when IM or SC administration modes are used the dosage is approximately 10 times that used for IV administration.

In accordance with a preferred embodiment of the invention, treatment of an individual with the active ingredient may be for the purpose of preventing restenosis before its occurrence. For prevention, the active ingredient may be administered to the individual before angioplasty procedure, during the procedure or after the procedure as well as combination of before, during and after procedural administration. Furthermore, the active ingredient may be administered via IV, IA, IM, SC, IP or any other suitable type of administration. For example, the active ingredient may be administered via IA the day of the angioplasty procedure (day 0), via IV the day before the procedure (−1) and/or on day 0, or both via IV the day before the procedure (−1) and also after the procedural administration, for example, on day 6.

In accordance with a further embodiment of the invention, the active ingredient is administered to an individual suffering from restenosis for the purpose of reducing or treating restenosis. In such a case, the active ingredient may also be administered to the individual at different periods of time after restenosis is discovered, either alone or in combination with other kinds of treatments.

In addition, the active ingredient may be administered before any other conditions which may yield accelerated arteriosclerosis, as well as acutely after the process has begun to inhibit further development of the condition.

EXAMPLES

The invention will now be demonstrated by way of non-limiting examples with reference to the accompanying drawings. The animal models used in the examples below include the balloon-injured rat carotid arterial model and the balloon-injured hypercholesterolemic rabbit carotid arterial model. The rat is an acceptable model in evaluating the antirestenotic effects of drugs and composites; however, the rabbit is more preferred since it, unlike the rat, is both atherosclerotic and contains a significant number of macrophages in the arterial wall.

Example 1

Liposomes of Clodronate

Stock solutions of clodronate were prepared by dissolving the drug in deionized water at a concentration of 0.11 M, pH=7.

Liposome Preparation 38.9 mg of distearoylphosphatidylglycerol (DSPG), 118.5 mg of distearoyl-phosphatidylcholine (DSPC) and 38.7 mg of cholesterol were accurately weighed and dissolved in 20 ml of chloroform: methanol (9:1) in a round bottom vial. The vial was gently warmed, and the solvent was then evaporated in rotavapor. 20 mls of hydrated diisopropylether were then added and the vial was put into a water bath until the contents were dissolved. 8 mls of the clodronate solution prepared as described above were then added, and the solution was sonicated at 55° C. for a period of 45 minutes. The organic phase was then evaporated in rotavapor (55° C., 100 rpm). Similarly, other drug-containing liposomes can be prepared.

Purification of Prepared Liposomes

A Sephadex gel was prepared by dissolving 2.6 grams of Sephadex G-50 in 40 mls of water and stabilizing overnight. The column was rinsed with 100 mls of buffer (50 mM Mes+50 mM HEPES+75 mM NaCl, pH 7.2). The liposomes were applied to the column and the column was rinsed with the buffer. The liposome was seen as a band which can be followed in the column by its color. About 20 drops were collected from the column into each tube.

Animals

Animals were obtained and housed in the animal facilities of the Faculty of Medicine, The Hebrew University of Jerusalem, conforming to the standards for care and use of laboratory animals of the Hebrew University of Jerusalem. Male rats of Sabra strain weighing 350–420 g were used. The animals were fed standard laboratory chow and tap water ad libitum. All in vivo experiments were conducted under general anaesthesia achieved with 80 mg/kg ketamine and 5 mg/kg xylazine administered IP.

Rat Carotid Catheter Injury Model

The distal left common and external carotid arteries were exposed through a midline incision in the neck. The left common carotid artery was denuded of endothelium by the intraluminal passage of a 2F balloon catheter introduced through the external carotid artery. The catheter was passed three times with the balloon distended sufficiently with saline to generate a slight resistance. The catheter was then removed and the external carotid artery was ligated, and the wound was closed with surgical staples.

Seven rats served as the control group, and 6 rats as the treated group (randomly chosen). Liposomal clodronate was injected IV to the "treated group" one day prior to the arterial injury (6 mg of clodronate per rat) and repeated on day 6. In the control group similar injections were administered but with "empty" or blank liposomes (no clodronate).

All animals were sacrificed 14 days after injury by an overdose of pentobarbital. Arteries were perfusion-fixed with 150 ml of 4% formaldehyde solution pH 7.4 at 100 mm Hg. The right atrium was dissected and an 18G catheter connected to the perfusion system was inserted in the left ventricle. The arterial segments were dissected, cut, gently separated from the polymer, and postfixed for at least 48 hours in the same fixative solution. The arterial segments were embedded in paraffin and cut at 8–10 sites 600 $\mu$m apart. Sections of 6 $\mu$m were then mounted and stained with Verhoeffs elastin stain for histologic examination.

Morphometric Analysis

The slides were examined microscopically by an investigator blinded to the type of the experimental group. Six to eight sections in each slide were evaluated by computerized morphometric analysis and the averaged section data were further used as a representative of a whole slide for comparisons between groups. The residual lumen, the area bounded by the internal elastic lamina (original lumen), and the area circumscribed by the external elastic lamina ("total arterial area") were measured directly. The degree of neointimal thickening was expressed as the ratio between the area of the neointimal and the original lumen (% stenosis), and as the ratio between the neointimal area to the area of the media (N/M). The medial area, an indirect index of SMC viability, was determined as the difference between the total arterial area and the original lumen area.

The surgical procedure and treatment did not cause mortality or apparent morbidity of the animals.

Figure 1:
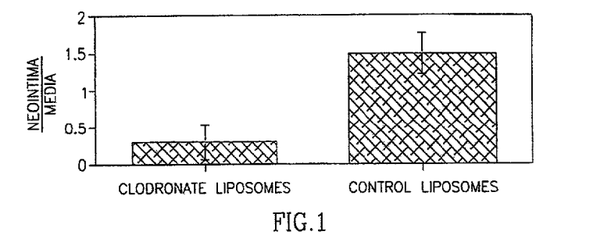
FIGS. 1–3 are bar graphs of results demonstrating the effect of clodronate encapsulated in liposomes on the reduction of restenosis in an experimental rat carotid catheter injury model as compared to the effect of control liposomes which did not contain clodronate on the same rats. In these figures.
Figure 2:
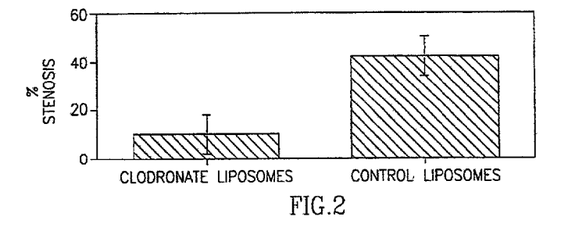
Figure 3:
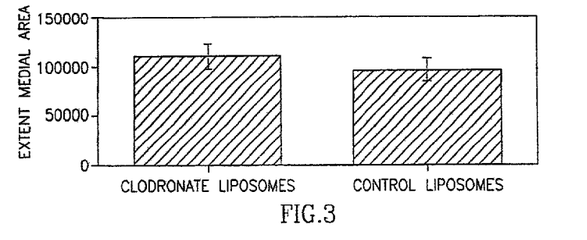

As seen in FIG. 1 the ratio between the neointimal area to the area of the media (N/M) was significantly reduced following treatment with clodronate-encapsulated in liposomes. The N/M ratio in clodronate treated rats was $0.28\pm0.23$ as compared to $1.42\pm0.26$ in the control group (mean$\pm$SD, p<0.01). Similarly as seen in FIG. 2, significant inhibition of % stenosis was achieved in the treated group: $9.8\pm7.76$ vs. $41.53\pm7.9$, treated and control groups, respectively (mean$\pm$SD, p<0.01). There were no apparent systemic side effects nor any effects on somatic growth as illustrated in FIG. 3.

Thus, the results of the experiments indicate that treatment of rats with clodronate-containing liposomes significantly reduces restenosis observed as neointimal formation following balloon-injury of the carotid artery.

Example 2

The antirestenotic effects of liposomal clodronate injections were studied in the balloon-injured rat and hypercholesterolemic rabbit carotid arterial models. The rats were treated by clodronate-containing liposomes, empty liposomes (control), and clodronate in solution (additional control). The dose of clodronate injected was 1.5 and 15 mg/kg administered one day before procedure (−1) and/or on day 6 (+6) post injury. The rabbits (following 30 days of atherosclerotic diet) were treated one day prior to balloon angioplasty by liposomal clodronate (10 mg/kg). The lumen, neointimal, medial and vessel areas and volumes were measured in the treated and control animal groups by digital planimetry of histological sections, at 14 and 30 days post injury in the rat and rabbit models, respectively.

Figure 4:
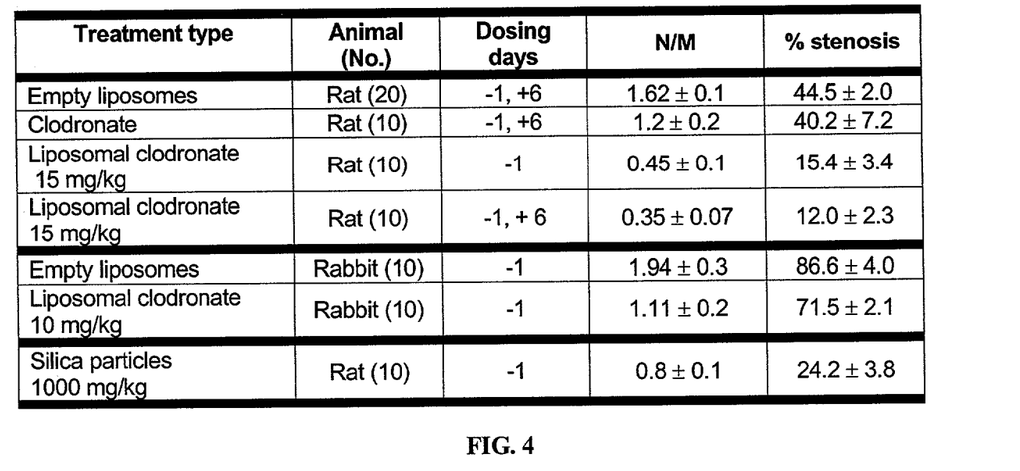
FIG. 4 illustrates the antirestenotic effects of liposomal clodronate in the balloon-injured rat and atherosclerotic rabbit carotid arterial models.

The results of the antirestenotic effects of liposomal clodronate are shown in FIG. 4. As illustrated, no significant differences were found between treatments with empty liposomes, and free clodronate in solution, which both exhibited marked neointimal formation. The extent of mean neointimal formation, mean neointimal to media ratio (N/M), and % stenosis following treatment with clodronate-laden liposomes was significantly reduced. However, the medial area was not affected by the various treatments indicating no deleterious effects on quiescent cells. Moreover, there were neither apparent systemic side effects nor any effects on bone and somatic growth. Significantly, more potent treatments were evaluated, specifically, 1×15 mg/kg (−1) and 2×15 mg/kg (−1, and +6) injections, with no significant difference between them. Similar findings of no adverse effects were also observed in the rabbits' study. Liposomal clodronate was significantly effective in reducing neointimal formation and % stenosis.

Furthermore, injection of silica particles also reduces intimal formation (FIG. 4). This observation can be attributed to the known inhibiting effect of silica on macrophages.

The results of the experiment indicated that treatment by clodronate-containing liposomes significantly reduces neointimal formation following balloon-injury both in rat and rabbit models. There were neither apparent systemic and local side effects nor any effects on somatic growth. It should be noted that although BPs are known as affecting bone, no effects on the bone or on calcium and phosphorus levels in bone and blood were observed following treatment with liposomal preparation of clodronate.

Example 3

Effect of Liposomal Clodronate on IL-1$\beta$ Production and Transcription and MMP-2 Activity The effects of liposomal clodronate on interleukin 1-$\beta$ (IL-1$\beta$) production and transcription and matrix metalloproteinase-2 (MMP-2) activity were studied in the balloon-injured rat and the hypercholesterolemic rabbit carotid arterial models. A group of male Sabra Rats was prepared according to the rat carotid catheter injury model described supra, in Example 1. The hypercholesterolemic rabbit model consisted of New Zealand White rabbits weighing 2.5–3.5 kg. The rabbits were fed an atherogenic diet of 2% cholesterol and 6% peanut oil starting 30 days before angioplasty and hypercholesterolemia was established (plasma cholesterol>1,200 mg/dL). The rabbits were then anesthesized by xylazine (7 mg/kg) and ketamine (40 mg/kg). Heparin (200 units/kg), atropine (0.05 mg) and norfloxacin nicotinate (70 mg) were also administered to the rabbits. Thereafter, balloon injury was performed on the left common carotid artery with a 3 mm angioplasty balloon catheter (Cordis, Miami, Fla., USA, 2×1 min inflation at 8 atm). In both the rabbit and rat models, liposomal clodronate (LC) was injected IV to the "treated group" both one day prior to the arterial injury (−1d) and six days after (+6) at a dosage of 15 mg/kg. The control animals were treated with empty liposomes, i.e., liposomes with no bisphosphonates encapsulated therein.

IL-1β Production and Transcription

Arteries and livers were homogenized in collagenase buffer (5 mM $CaCl_2$, 50 mM Tris, 0.02% Brij 35, 0.2 M NaCl, pH 7.6). IL-1β was measured using commercial ELISA kits (R&D Systems, Minneapolis, Minn., USA). For RT-PCR analysis, RNA from the carotid arteries was extracted using a RNA isolation kit. (Life Technologies Inc., USA). Quality, size and quantity of RNA were examined by conventional 1.0% agarose gel electrophoresis (Sigma) and spectrophotometry. Total RNA (2 µg) was used for the synthesis of first strand cDNA using Superscript reverse transcriptase and a mixture (1:1) of oligo (dT) and random hexanucleotides in 20 ml reaction volume. First strand cDNA was amplified by PCR. To ensure the quality of the RNA preparation and to normalize the RT-PCR protocol, β-actin RT-PCR products were also produced for all samples. cDNA (2 µl) was added to a 50 ml reaction mixture containing 5 µl 10*PCR reaction buffer, 2.0 mM $MgCl_2$, 20 mM of each dATP, dCTP, dGTP, and dTTP, 200 nM of each oligonucleotide primer, and 1.0 unit Taq DNA polymerase. Oligonucleotide primers for rabbit IL-1β and β-actin were synthesized based on the following nucleotide sequences: IL-1β sense primer 5'-TAC AAC AAGAGC TTC CGG CA (SEQ. ID. NO. 1); IL-1beta antisense primer 5'-GGC CAC AGG TAT CTT GTC GT (SEQ. ID. NO. 2); β-actin sense primer 5'-ACG TTC AAC ACG CCG GCC AT (SEQ. ID. NO. 3); β-actin antisense primer 5'-GGA TGT CCA CGT CGC ACT TC (SEQ. ID. NO. 4). Amplification was performed using a DNA thermal cycler for 37 cycles, where a cycle profile consisted of 1 minute at 94° C. for denaturation, 1 minute at 55° for annealing, and 1 minute at 72° for extension. The size of amplified fragments was 354 and 493 bp for IL-1β and β-actin, respectively. Electrophoresis of 10 µl of the reaction mixture on a 1.5% agarose gel containing ethidium bromide was performed to evaluate amplification and size of generated fragments. PCR marker (Promega, USA) was used as a standard size marker. The bands' intensity was quantified by densitometry, and values of the bands were normalized to β-actin mRNA expression.

MMP-2 Activity

The supernatant of arteries homogenate in collagenase buffer (see above) was analyzed for collagenase activity. Samples of arteries were separated on gelatin-impregnated (1 mg/ml: Difco, Detroit, Mich., USA) SDS 8% polyacrylamide gels under non-reducing conditions, followed by 30 minutes of shaking in 2.5% Triton X-100 (BDH, Poole, UK). The gels were incubated for 16 hours at 37° C. in a collagenase buffer, and stained with 0.5% Coomassie G-250 (BioRad, Richmond, Calif.) in methanol/acetic acid/$H_2O$ (30:10:60). Band intensity was determined by computerized densitometry (Molecular Dynamics type 300A).

Figure 5:
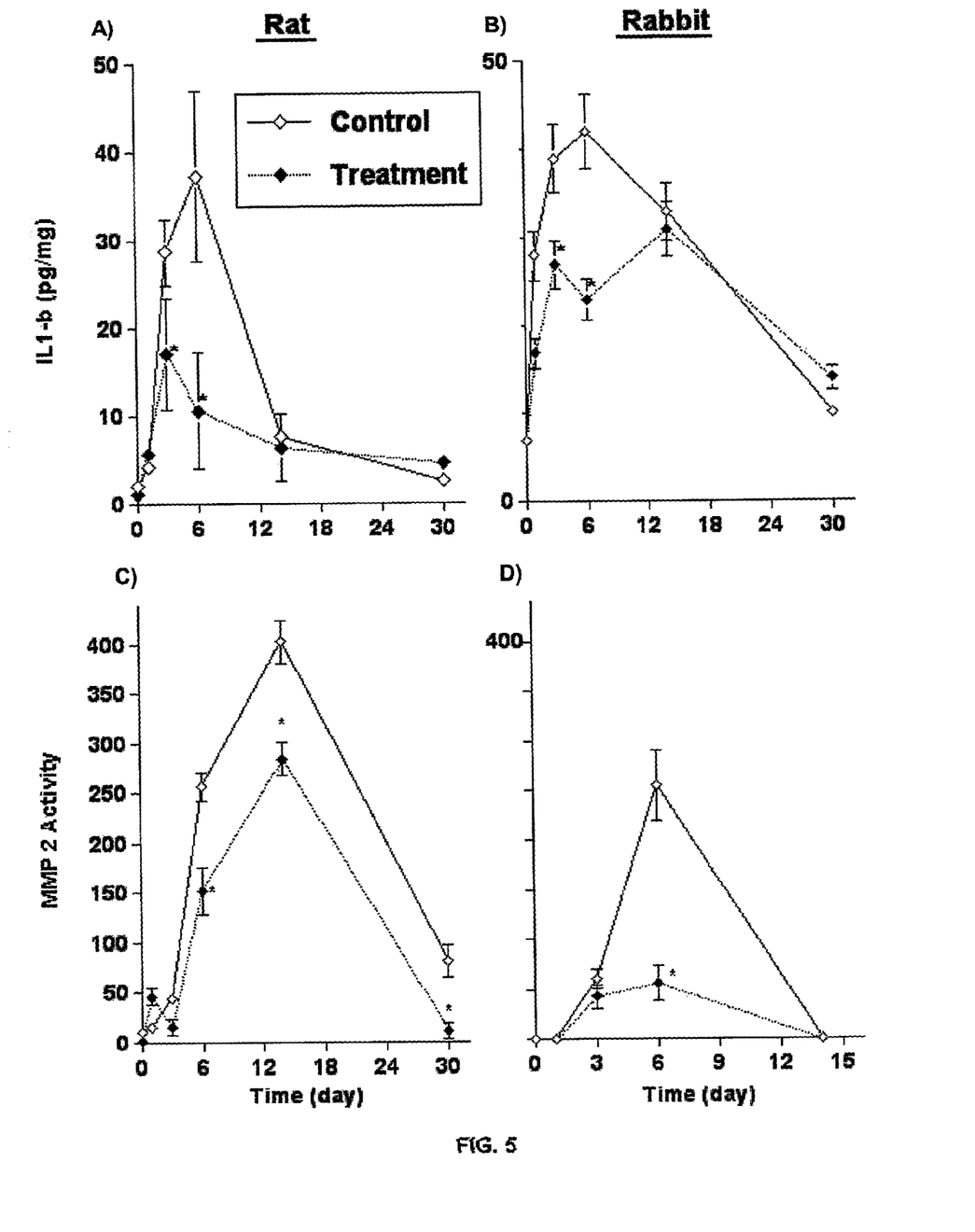
FIGS. 5a, 5b, 5c and 5d illustrate the effect of liposomal clodronate treatment on interleukin 1-β (IL-1β) concentration and matrix metalloproteinase-2 (MMP-2) activity in the arteries of rats and rabbits following balloon injury. Specifically.

As illustrated in FIG. 5A, analysis of IL-1β levels in rat arterial tissue following balloon injury (control animals) revealed a bell shape pattern peaking at 6 days following injury (37.3±9.6 pg/mg protein) and returning to basal levels after 30 days. However, a significant decrease of IL-1β levels was observed on days 3 and 6 post-injury, following LC-treatment. As illustrated in FIG. 5B, a similar response was observed in the rabbit artery, with a significant decrease of IL-1β levels on days 2, 4 and 6 post-injury, following LC-treatment.

Figure 6:
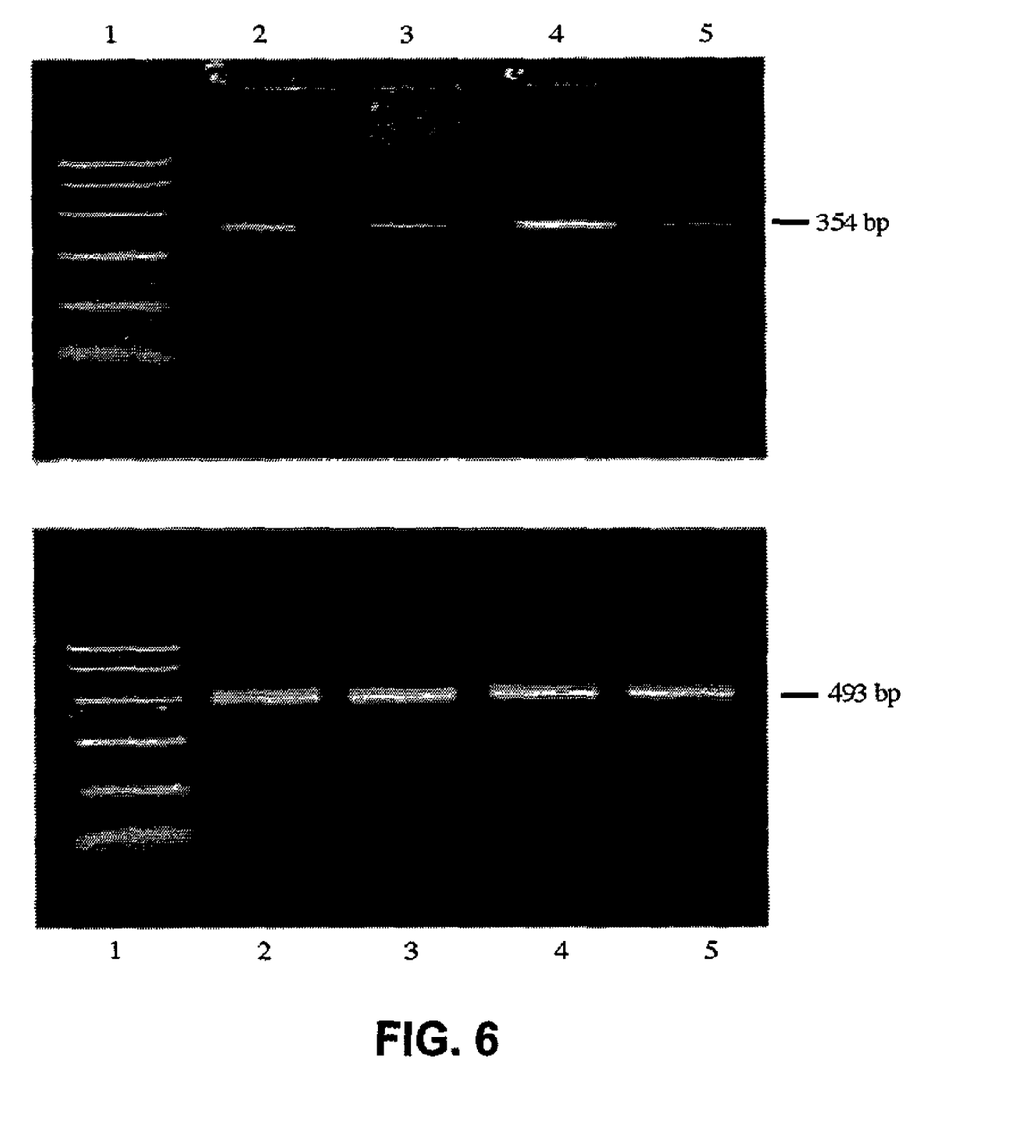
FIG. 6 illustrates the effect of liposomal clodronate on IL-1β transcription in rabbits' arteries following balloon injury.

The reduction in arterial IL-1β levels following LC-treatment was associated with a marked decrease in IL-1β transcription. IL-1β mRNA transcription in rabbits' arteries was analyzed following LC-treatment, which was administered the day before balloon injury (−1). The gel electrophoresis of the resultant reaction mixture following RT-PCR analysis is illustrated in FIG. 6. The RT-PCR analysis illustrates that in control animals (no treatment with LC), IL-1β mRNA transcription was stronger three days after the injury (+3) than one day after the injury (+1). However, IL-1β transcription on both day one (+1) and day three (+3) after the injury, was significantly reduced by LC treatment. In FIG. 6, Lane 1 represents PCR markers (50, 150, 300, 500, 750, 1000 bp); lanes 2 and 3 represent LC-treated and untreated (control), on day +1, respectively; and lanes 4 and 5 represent LC-treated and untreated (control), on day +3, respectively. Note the strong signal (at 354 bp) of IL-1β mRNA expression in untreated (control) animals (lanes 2 and 4) that was suppressed by LC treatment (lanes 3 and 5). Expression of β-actin mRNA expression (493 bp) was used as loading control in the same samples (lower panel). IL-1β mRNA levels (densitometry analysis relative to β-actin mRNA) were found to be 0.45±0.24 and 0.37±0.44 on day +1, 0.59±0.2 and 0.12±0.1 on day +3, LC-treated and untreated animals, respectively (3 independent RT-PCR reactions).

Additionally, IL-1β levels in the liver were also examined. A significant reduction was noted after a single injection of LC on day −1 inclining to basal levels at 30 days (data not shown).

As illustrated in FIG. 5c, MMP-2 activity in rats' arterial tissue increased following injury, exhibiting a bell shape pattern peaking at 14 days (252±12 and 402±44, at 6 and 14 days, respectively), and returning to basal levels at 30 days. However, treatment with LC resulted in a significant reduction of MMP-2 activity at 6 and 14 days (152±23 and 284±17, respectively). Similarly, in the rabbit's artery, the surge of MMP-2 activity was less than that of the rat's artery, but the effect of LC-treatment was more pronounced (See, FIG. 5d). As illustrated in FIG. 5d, MMP-2 activity at 6 days was 248±42 and 52±5, in control and LC-treated rabbits, respectively, returning to the baseline approximately 14 days after injury.

Example 4

Effect of Liposomal Clodronate on PDGF-BB, PDGFβR and PDGFβR Tyrosine Phosphorylation The effect of liposomal clodronate on PDGF-BB, platelet-derived growth factor β receptor (PDGFβR) and PDGFβR tyrosine phosphorylation was studied in the balloon-injured rat arterial model. A group of male Sabra Rats was prepared according to the rat carotid catheter injury model described supra, in Example 1. Carotid arteries were rapidly retrieved before injury and at day 14, rinsed in cold PBS and immediately deep-frozen (−70° C.) until further processing. Frozen segments were mechanically minced on dry ice. There was a total of 12 animals in each group, with four arteries being pooled for each run. Liposomal clodronate (LC) was injected IV to the "treated group" one day prior to the arterial injury (−1d) and six days later (+6) at a dosage of 15 mg/kg. Proteins were extracted using lysis buffer (150 mM NaCl, 50 mM Tris-HCl, 1% Triton X-100, 10 mM EDTA, 1 mM PMSF, 100 μM sodium orthovanadate and 1% aprotinin) and pooled for 4 animals in each group. Protein content was determined using a modified Lowry protocol, and samples of 100 μg were subjected to SDS-PAGE (7.5% or 12%) and blotted onto a nitrocellulose membrane (Hybond C extra, Amersham) of PVDF membrane (Roth) for the analysis of PDGFβR or PDGF-B chain, respectively. PDGFβR protein was detected using a polyclonal antibody (SC-431, Santa Cruz, USA) and a polyclonal alkaline phosphatase-conjugated goat anti rabbit antiserum (Tropix, USA), and tyrosine phosphorylated proteins were detected using a mixture of monoclonal antibodies PY20 (Transduction Laboratories, USA) and 4G10 (UBI, USA) followed by the application of a chemoluminescence-based detection system including a polyclonal alkaline phosphatase-conjugated anti-mouse antiserum (CDP Star, TROPIX). PDGF-BB protein was detected using the monoclonal antibody PGF007 (Mochida), a horseradish-conjugated rabbit anti-mouse antiserum (DAKO) and the detection system Super Signal Ultra (Pierce, Germany). Quantification of the data was made by means of LAS-1000 Imager (Fuji, Japan).

Figure 7:
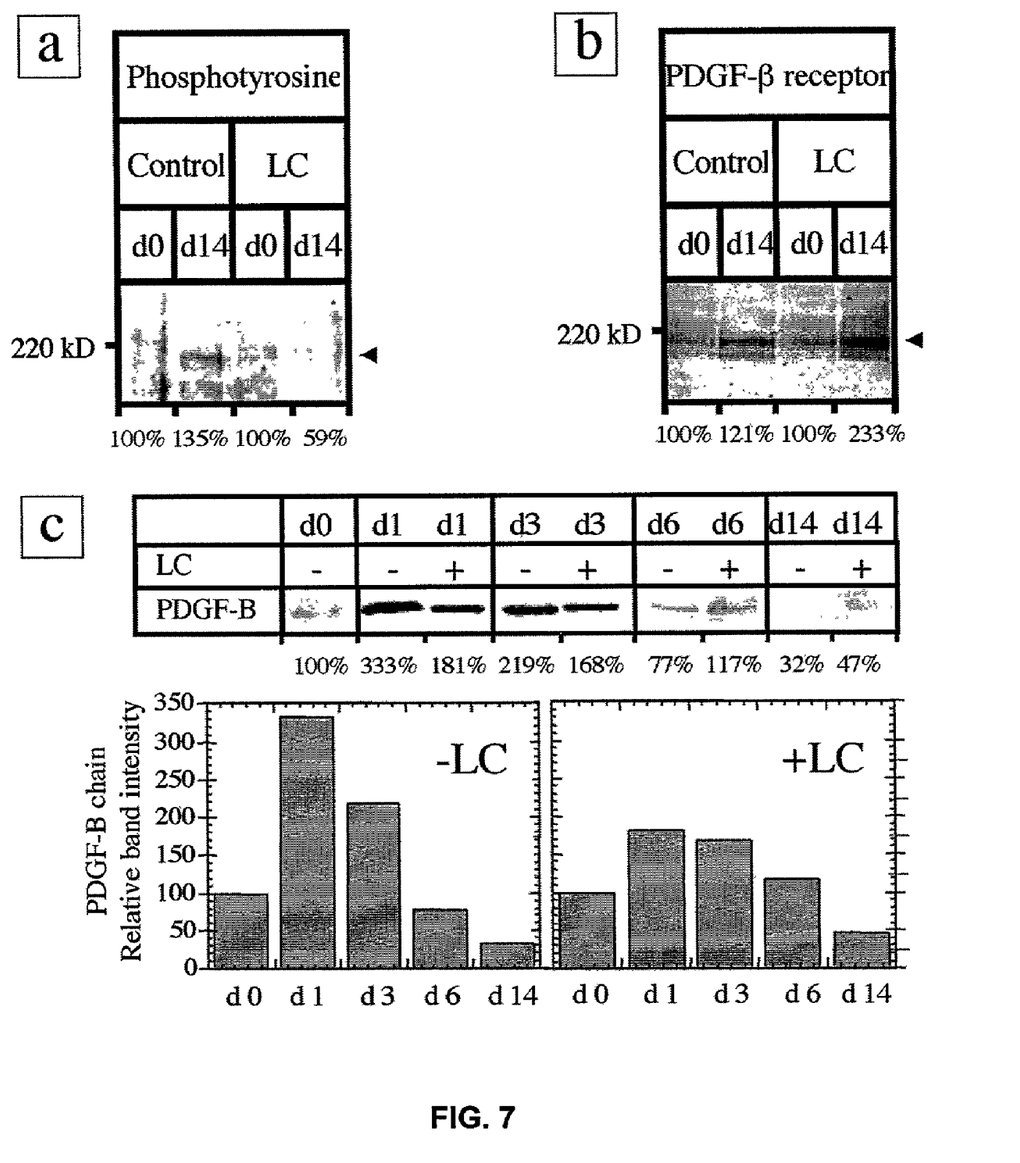
FIGS. 7a, 7b, and 7c illustrate the effect of liposomal clodronate treatment on the platelet-derived growth factor (PDGF) system in the arterial walls of rats following balloon injury. Specifically.

As illustrated in FIG. 7a, the activation of PDGFβR (i.e., tyrosine phosphorylation) markedly increased to 135% of the baseline levels in the balloon-injured artery of untreated rats, while it was barely detectable in LC treated rats, i.e. below baseline activity. Note the band representing activated PDGFβR at 190 kDa. Additionally, as depicted in FIG. 7b, vascular injury resulted in the upregulation of PDGFβR protein both in the untreated group (121%) and the LC-treated group (233%). Injury resulted in a strong accumulation of PDGF-B protein within the vessel wall on days 1 and 3 after injury (46 kDa), reaching 333% and 219% of the baseline level, respectively (FIG. 7c). Further illustrated in FIG. 9c is that in LC-treated rats, this accumulation of PDGF-B was strongly reduced (181% and 168%, on days 1 and 3, respectively), in correlation with the reduced activation of PDGFβR at these time points.

The results of the experiments described supra, clearly indicate that treatment of rats and rabbits with liposomal clodronate significantly reduces the transcription and production of interleukin 1-β, the activity of matrix metalloproteinase-2, the activation of platelet-derived growth factor β receptor (PDGFβR), and the levels of PDGF-B protein.

We claim:

1. A method of decreasing or inhibiting the activity or production by blood monocytes of cytokines or growth factors, the cytokines or growth factors being associated with vascular restenosis, comprising administering to an individual in need thereof an effective amount of an insoluble particle comprising an active ingredient selected from the group consisting of a bisphosphonate, a bisphosphonate salt, a bisphosphonate ester, and a bisphosphonate complex, wherein the active ingredient is encapsulated in, embedded in, absorbed onto, or linked to a particle having a size within the range of 0.01–1.0 μm, thereby treating or inhibiting restenosis.

2. A method of decreasing or inhibiting the activity or production by blood monocytes of cytokines or growth factors, the cytokines or growth factors being associated with vascular restenosis, comprising administering to an individual in need thereof an effective amount of an insoluble particulate comprising an active ingredient selected from the group consisting of a bisphosphonate, a bisphosphonate salt, a bisphosphonate ester, and a bisphosphonate complex, wherein the insoluble particulate has a diameter within the range of 0.01–1.0 μm, thereby treating or inhibiting restenosis.

3. The method according to claim 1 or 2, wherein the cytokines and growth factors are selected from the group consisting of interleukin 1-β, matrix metalloproteinase-2 (MMP-2), and platelet-derived growth factor β (PDGFβ).

4. The method according to claim 1, wherein the insoluble particle is selected from the group consisting of polymeric particles, liposomes, microparticles, nanoparticles, microspheres, and nanospheres.

5. The method according to claim 2, wherein the insoluble particulate is selected from the group consisting of aggregates, flocculates, colloids, polymer chains, insoluble salts, and insoluble complexes.

6. The method according to claim 1, wherein the active ingredient is encapsulated within the particle.

7. The method according to claim 1, wherein the active ingredient is embedded within the particle.

8. The method according to claim 1, wherein the active ingredient is adsorbed on the particle surface.

9. The method according to claim 1 or 2, comprising administering to the individual an active ingredient, having the following formula (I):

wherein $R_1$ is H, OH or a halogen atom; and $R_2$ is a halogen; liner or branched $C_1$–$C_{10}$ alkyl or $C_3$–$C_8$ alkenyl optionally substituted by heteroaryl or heterocyclyl $C_1$–$C_{10}$ alkylamino or $C_3$–$C_8$ cycloalkylamino where the amino may be a primary, secondary, or tertiary; —NHY where Y is hydrogen, $C_3$–$C_8$ cycloalkyl, aryl or heteroaryl; or $R_2$ is —SZ where Z is chlorosubstituted phenyl or pyridinyl.

10. The method according to claim 1 or 2, wherein said active ingredient is clodronate, etidronate, tiludronate, pamidronate, alendronate, risendronate, or 2-(2-aminopyrimidinio) ethylidene-1, 1-bisphosphonic acid betaine (ISA-13-1).

11. The method according to claim 1 or 2, wherein the administration is intravenous (IV), intrarterial (IA), intramuscular (IM), subcutaneous (SC), intraperitoneal (IP), or delivered by a 'sweating balloon,' a coated balloon or on a coated stent.

12. The method according to claim 1 or 2, wherein the active ingredient is administered before an angioplasty procedure.

13. The method according to claim 1 or 2, wherein the active ingredient is administered the day of an angioplasty procedure.

14. The method according to claim 1 or 2, wherein the active ingredient is administered after an angioplasty procedure.

15. A method of decreasing or inhibiting the activity or production by blood monocytes of cytokines or growth factors, the cytokines or growth factors being associated with vascular restenosis, comprising administering to an individual in need thereof an effective amount of a liposomal clodronate having a diameter within the range of 0.01–1.0 µm, thereby treating or inhibiting restenosis.

16. A method of decreasing or inhibiting the activity or production by blood monocytes of cytokines or growth factors, the cytokines or growth factors being associated with vascular restenosis, comprising administering to an individual in need thereof an effective amount of an insoluble bisphosphonate nanoparticle having a diameter within the range of 0.01–1.0 µm, thereby treating or inhibiting restenosis.

17. A method of decreasing or inhibiting the activity or production by blood monocytes of cytokines or growth factors, the cytokines or growth factors being associated with vascular restenosis comprising administering to an individual in need thereof an effective amount of a liposomal alendronate having a diameter within the range of 0.05–0.20 µm thereby treating or inhibiting restenosis.

* * * * *